United States Patent [19]

Black

[11] Patent Number: 5,479,543
[45] Date of Patent: Dec. 26, 1995

[54] PRECISION LIGHT-GUIDING TERMINAL FOR OPTICAL FIBERS

[75] Inventor: Michael Black, Foster City, Calif.

[73] Assignee: Reliant Technologies, Inc., Foster City, Calif.

[21] Appl. No.: 252,913

[22] Filed: Jun. 2, 1994

[51] Int. Cl.⁶ .................................................. G02B 6/26
[52] U.S. Cl. ............................ 385/31; 385/37; 385/139
[58] Field of Search ................................. 385/15, 31, 33, 385/34, 37, 38, 39, 76, 139

[56] References Cited

U.S. PATENT DOCUMENTS

| | | | |
|---|---|---|---|
| 4,068,121 | 1/1978 | Bringhurst et al. | 385/37 X |
| 4,883,333 | 11/1989 | Yanez | 385/33 |
| 4,993,796 | 2/1991 | Kapany et al. | 385/31 X |
| 5,074,632 | 12/1991 | Potter | 385/31 |
| 5,093,877 | 3/1992 | Aita et al. | 385/34 |
| 5,202,950 | 4/1993 | Arego et al. | 385/33 X |
| 5,303,324 | 4/1994 | Lundahl | 385/34 X |

*Primary Examiner*—John D. Lee

[57] ABSTRACT

A precision light-guiding terminal for optical fibers or optical fiber bundles consisting of a terminal (34) with an insertion duct (28) for receiving the end portion of an optical fiber (20) or optical fiber bundle (52), an input face (30) for in-coupling of a light (38) guided by the optical fiber (20) or optical fiber bundle (52), a light-guiding tip (40) for shaping guiding and performing optical operations on the light (38), and an output face (42) for out-coupling of the light (38).

9 Claims, 4 Drawing Sheets

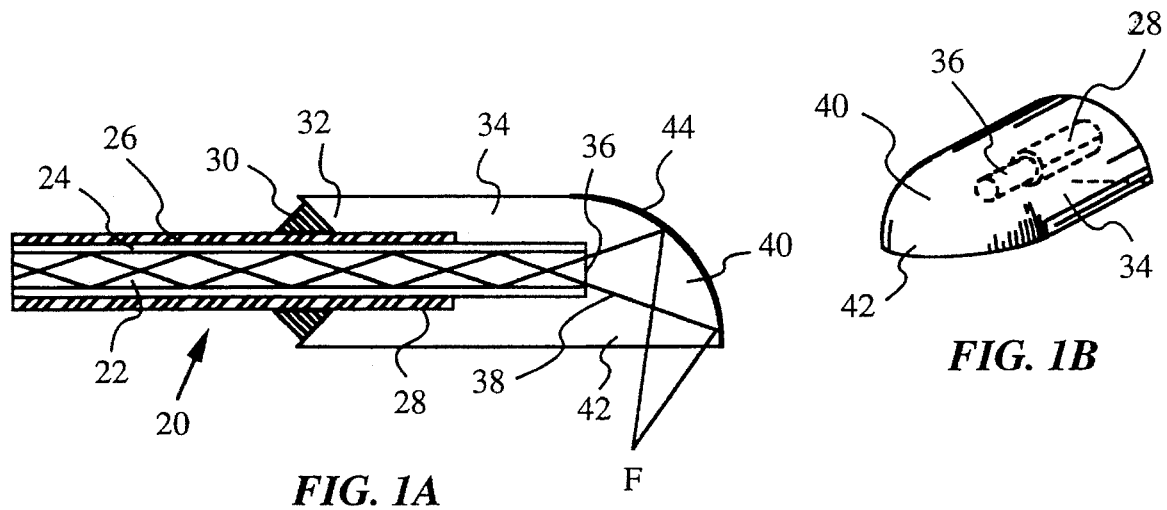
FIG. 1A
FIG. 1B
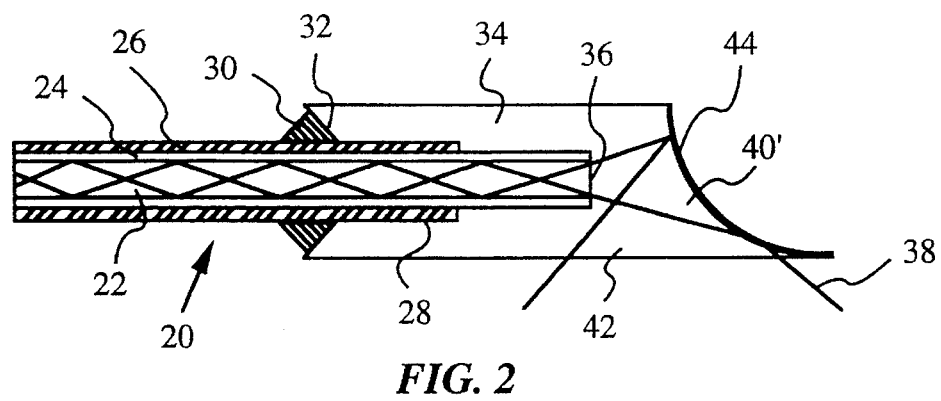
FIG. 2
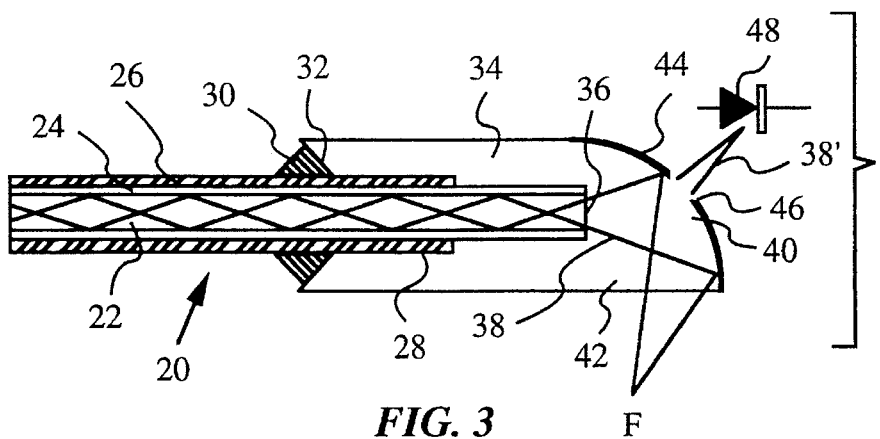
FIG. 3

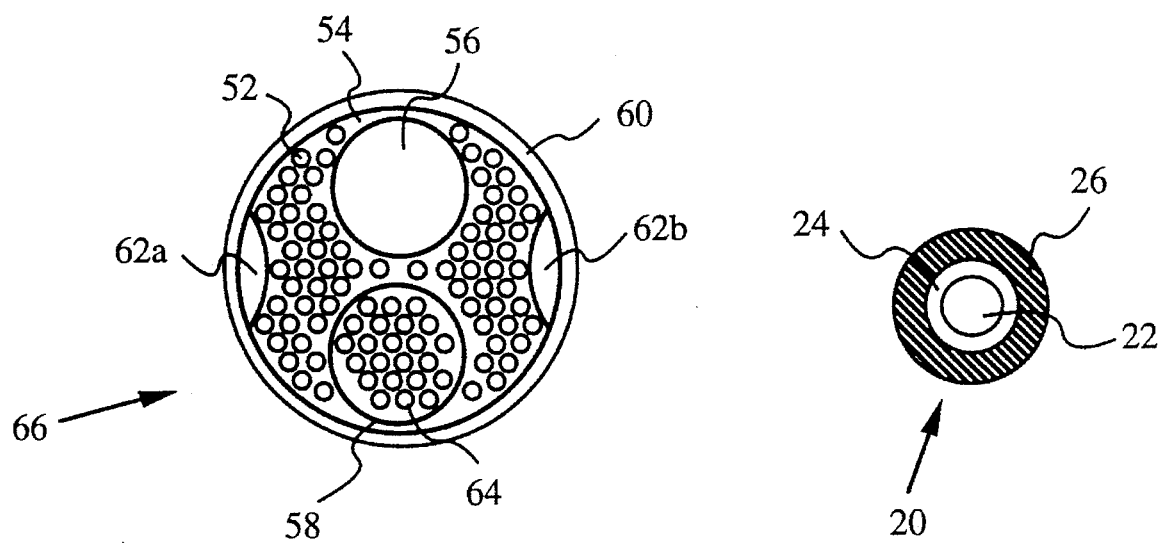
FIG. 10     FIG. 11
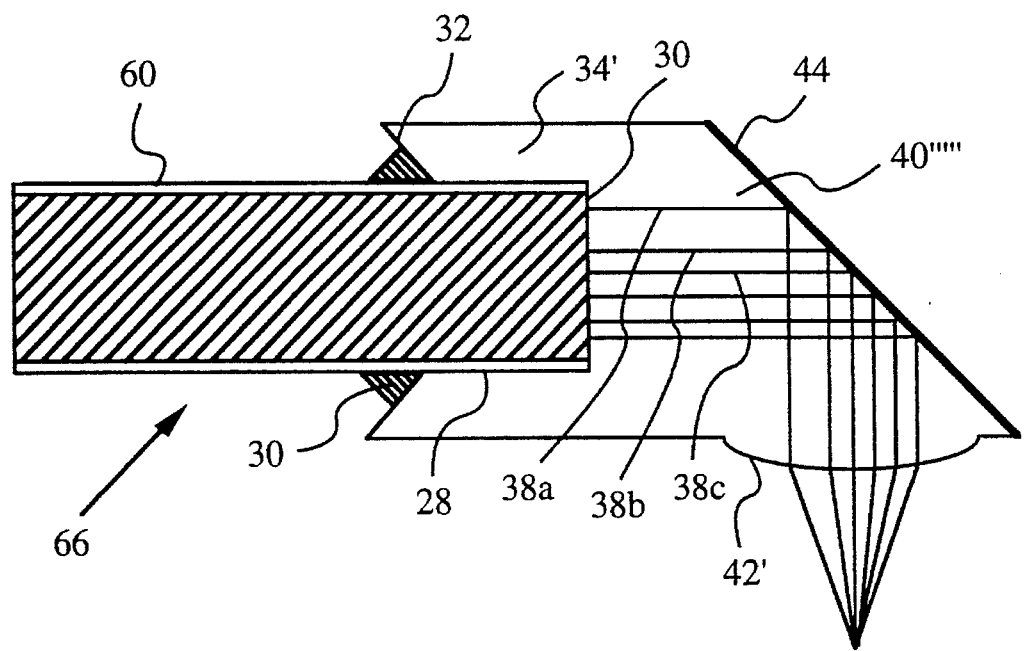
FIG. 12

PRECISION LIGHT-GUIDING TERMINAL FOR OPTICAL FIBERS

BACKGROUND—FIELD OF THE INVENTION

The present invention relates to the field of fiber optics, and in particular to guiding and focussing of light delivered by optical fibers.

BACKGROUND—DESCRIPTION OF PRIOR ART

Optical fibers are used to deliver various types of light for a wide range of applications. For example, optical fibers conduct high-energy laser light for cutting and vaporizing construction materials, performing laser surgery on human and other animal tissue, etching precision templates, etc. Lower-energy laser light carrying telecommunication or computer data can be transmitted by optical fibers between senders and receivers. Finally, non-laser light can be transported with the aid of optical fibers as well.

An optical fiber normally consists of a central core portion made of a transparent, low-energy loss material with a high refractive index, an intermediate layer and made of a material whose refractive index is lower than that of the core, and an outer or protective layer known as a buffer. The buffer can be made of various materials, e.g., plastic. Once light is injected into the fiber core at the inlet face end at a suitable angle of incidence, known as an acceptance angle, it will propagate inside the core toward a fiber outlet face end. Along its path the light will undergo numerous internal reflections at the interface between the core and the cladding. Finally, it will emerge at the outlet face end at the same angle in the form of a diverging beam.

Guiding and/or focussing the light emerging at the outlet end of an optical fiber has always presented technical problems. Traditional solutions include systems of reflectors, lenses, and other optical elements mounted on mechanical holding devices. In such systems proper beam guidance and/or focussing is ensured by displacing and rotating the optical elements with respect to each other. This cumbersome process requires much effort and time, especially in complex setups employing numerous optical elements. In addition, a great deal of care has to be taken to avoid misalignments.

Further, mechanical difficulties arise at the outlet end face of the optical fiber. The emerging light beam tends to melt the buffer which then obstructs the outlet face end. Removing the buffer remedies this problem but introduces another one by shifting the entire burden of mechanical support of the optical fiber to the cladding. The stress created by internal reflection of light guided in the core at the points where the buffer layer is stripped frequently causes the optical fiber to break. This problem is also encountered when splicing optical fibers, i.e., in situations where the light from one optical fiber is coupled into another fiber.

All the above-mentioned problems are compounded when guiding and focussing light emanating from several optical fibers. In this case the optical system requires even more elements, and alignment of the various output beams becomes very difficult. The problem is deeply felt in surgery, where no simple method exists to simultaneously guide and focus several laser beams for performing different kinds of incisions, e.g., a shallow cut and a deep one. Such treatment requires at least two precisely aligned laser beams focussed at two focal points.

OBJECTS AND ADVANTAGES OF THE INVENTION

In view of the above, several objects of the present invention are to provide a precision light-guiding terminal for optical fibers which eliminates the need for moving optical elements, ensures quick, easy, and precise beam alignment, and provides stress relief at fiber ends.

Other objects are to provide light-guiding terminal which is simple in construction, easy to replace, even by unskilled persons, and inexpensive.

Further objects are to provide light-guiding terminal which can receive many optical fibers or fiber bundles, which can precisely guide and focus all the light beams emanating from these fibers or bundles, and which permits manipulation of the shape, size, and location of the intersecting points between the various beams.

These and other objects and advantages will become more apparent after consideration of the ensuing description and the accompanying drawings.

SUMMARY OF THE INVENTION

Surprisingly, it has been found that a precision light-guiding terminal for optical fibers can be prefabricated in the form of a single rigid part. Such a light-guiding terminal consists of an insertion duct for receiving an end portion of an optical fiber, an input face for in-coupling of light conducted by the optical fiber, a tip portion for performing optical operations or shaping the in-coupled light, and an output face for out-coupling the shaped light. The optical operations performed by the tip are achieved with the aid of suitable geometrical curvatures of the tip portion of the light-guiding terminal, a reflective coating deposited on the light-guiding tip, and/or suitable diffraction gratings on the out-coupling face. The same technique can also be applied to optical fiber bundles.

BRIEF DESCRIPTION OF THE DRAWINGS

FIG. 1A is a side view of a light-guiding terminal for a single optical fiber with a convex focussing tip according to the invention.

FIG. 1B is a front view of the light-guiding terminal in FIG. 1A.

FIG. 2 is a side view of a light-guiding terminal for a single optical fiber with a concave dispersing tip according to the invention.

FIG. 3 is a side view of a light-guiding terminal for a single optical fiber with a convex focussing tip and photodetector according to the invention.

FIG. 10 is a cross section of an exemplary integrated optical cable which can be used with the light-guiding terminal of the invention.

FIG. 11 is a cross section of a single optical fiber used in optical fiber bundles.

FIG. 12 shows the optical cable line from FIG. 10 mounted in a light-guiding terminal.

LIST OF REFERENCE NUMBERS

Figure 4:
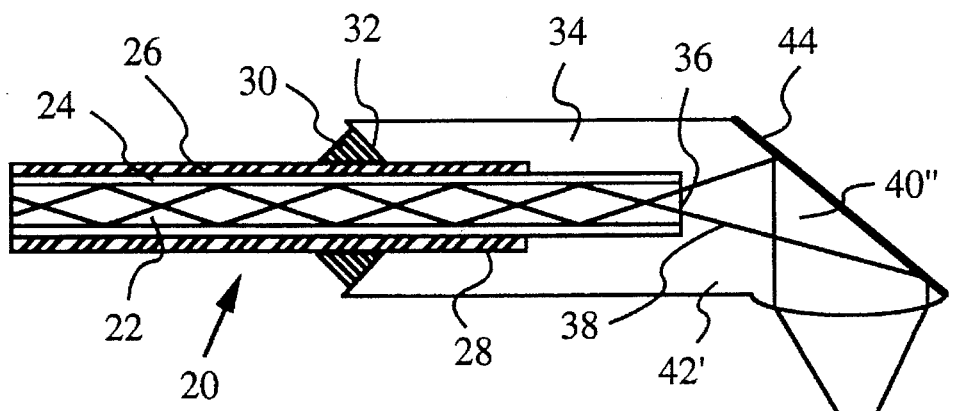
FIG. 4 is a side view of a light-guiding terminal for a single optical fiber with a planar reflecting tip and convex focussing face according to the invention.

| | |
|---|---|
| 20 (a, b, c) | optical fiber(s) |
| 22 | core |
| 24 | cladding |
| 26 | buffer |
| 28 (a, b, c) | insertion duct(s) |
| 30 | adhesive |
| 32 | conical space |
| 34, 34' | light-guiding terminal |
| 36, 36' | input face |
| 38 (a, b, c), 38' | light beam(s) |
| 40, 40' . . . | light-guiding tip |
| 42, 42' . . . | output face |
| 44 | reflective coating |
| 46 | outlet hole |
| 48 | photodetector |
| 50 | diffraction pattern |
| 52 | light-transmitter bundle |
| 54 | bonding epoxy resin |
| 56 | power laser fiber |
| 58 | video fiber bundle |
| 60 | protective sheath |
| 62a, 62b | fiber alignment pins |
| 64 | protective bundle collar |
| 66 | integrated optical cable |

DESCRIPTION OF LIGHT-GUIDING TERMINALS OF FIGS. 1A and 1B

A typical embodiment of a light-guiding terminal designed to receive light from a single optical fiber is shown in FIG. 1A. An optical fiber 20 has a core 22, a cladding 24, and a protective buffer 26. The end section of buffer 26 is stripped at the output end of optical fiber 20, as is commonly done in standard splicing applications. In the present embodiment less then 0.5 cm of cladding 24 remains exposed.

The stripped end portion of optical fiber 20 and a short intact section of fiber 20 rest snugly against the walls of an insertion duct 28 inside a light-guiding terminal 34. Terminal 34 is preferably molded of glass, plastic, silica, or other appropriate light-guiding material. In a preferred embodiment terminal 34 is made of a high-purity silica material, such as that, sold under the trademark Gelsil by Geltech, Inc., of Alachua, Fla. This material is very inexpensive and easily adaptable to arbitrary shapes through heat molding.

The walls of duct 28 are profiled in the shape of two coaxial, cylindrical sections, as shown in FIG. 1B. The diameter of the first cylindrical section of duct 28 corresponds to the diameter of optical fiber 20. The diameter of the second cylindrical section of duct 28 corresponds to the diameter of optical fiber 20 without buffer 26. In this embodiment both cylindrical sections of duct 28 are 0.5 cm long, Appropriate profiles of duct 28 permit the use of optical fibers stripped of longer or shorter buffer sections, e.g., from 0.1 mm to 5 cm, and having various cross sectional dimensions, e.g., from 0.01 mm to 1 cm and more.

The profile of duct 28 terminates in a planar input face 36. Input face 36 serves for in-coupling a light beam 38 transmitted through optical fiber 20 into terminal 34.

As shown in FIG. 1A, the left side of terminal 34 has a tapered entrance or conical space 32 where fiber 20 enters into duct 28 of terminal 34. A binding agent or adhesive 30 is provided inside space 32. For a secure coupling adhesive 30 should be chosen from among epoxy-based glues, or other adhesives commonly used to bond plastics and/or glass fibers. Otherwise, securement can be ensured by bracing, thermofusion, or other techniques in the field of bonding which are not detrimental to the elements of fiber 20.

The other end of terminal 34 is shaped in the form of a light-guiding tip 40. Tip 40 is convex and its surface is covered with a reflective coating 44. Appropriate choice of reflective coating 44 depends on the wavelength of light to be guided. In a preferred embodiment coating 44 consists of a silver-based metallic mirror coating capable of reflecting a wide range of light wavelengths, e.g., SIFLEX-MK II manufactured by Balzers Limited Film Section, FL-9496 of Lichtenstein. The area of reflective coating 44 and tip 40 are dimensioned so as to intercept the entire cross section of diverging light beam 38.

Furthermore, as shown in FIG. 1A, terminal 34 has a flat output face 42 for out-coupling of light beneath tip 40. A focal point F of converging light beam 38 is located below face 42. The distance between focal point F and face 42 depends upon the curvature of tip 40 and can generally vary within wide limits, e.g., from a fraction of a centimeter to several decimeters or much more, depending on intended use.

OPERATION OF LIGHT-GUIDING TERMINAL OF FIGS. 1A and 1B

To operate light-guiding terminal 34 shown in FIG. 1, stripped optical fiber 20 is first inserted into insertion duct 28. Then adhesive 30 is poured around fiber 20 to gel inside space 32. Once solidified, adhesive 30 holds fiber 20 securely in place while the walls of insertion duct 28 mechanically support the stripped section of fiber 20. This counteracts the large mechanical stress produced by light beam 38 reflecting inside core 22 at cladding 24 at the point where buffer 26 is removed.

After exiting from core 22 light beam 38 arrives at planar input face 36, through which it enters light-guiding terminal 34. Inside terminal 34 beam 38 propagates toward tip 40 in a diverging path. At tip 40 reflective coating 44 causes beam 38 to be reflected downward along a converging path. That is because tip 40 is convex in shape, thus acting like a focussing mirror. Continuing on its downward path, beam 38 exits tip 40 through output face 42 and converges at focal point F.

As already mentioned, the distance to focal point F will depend on the curvature of tip 40. Since the silica of tip 40 is very inexpensive and easy to heat mold, a large assortment of terminals 34 with different focal lengths can be produced and placed at the disposal of a technician mounting optical fibers. Consequently, proper focussing is ensured by appropriate choice of prefabricated terminal 34. No additional elements, such as adjusting mirrors, lenses, or any other optical elements are necessary.

DIVERGING-TYPE LIGHT-GUIDING TERMINAL—FIG. 2

FIG. 2 illustrates an alternative embodiment of terminal 34. The construction and form of terminal 34 are basically the same as in FIG. 1A with the exception that light-guiding tip 40' is concave. Once again, as in the above embodiment, tip 40' has the same reflective coating 44.

Terminal 34 shown operates in a similar manner as the one described above, but because of its concave tip 40' it uniformly disperses light beam 38 exiting through output face 42. Again, a proper choice of curvature will ensure desired divergence of emerging beam 38.

LIGHT-GUIDING TIP WITH LIGHT MEASUREMENT CAPABILITY—FIG. 3

FIG. 3 illustrates still another embodiment. In this one, reflective coating 44 covers entire tip 40 of terminal 34 with the exception of an outlet hole 46 located in the path of light beam 38. Hole 46 is small enough to leak a portion of light beam 38 in the form of a beam 38'. Typically, the diameter of hole 46 can be 1 mm or less. A photodetector 48, preferably a standard photodiode or a phototransistor, is positioned in the path of light which passes through hole 46. Photodetector 48 is connected to appropriate circuit elements, e.g., amplifiers, counters, etc. (not shown), to register light leaked through hole 46.

Terminal 34 shown in FIG. 3 functions just like the one illustrated in FIG. 1, but, in addition, passes a portion of light beam 38 through outlet hole 46. The light traversing hole 46 impinges upon photodetector 48 and is thus detected.

This event is registered by an electrical circuit (not shown) to which photodetector 48 is directly hooked up. Such monitoring enables an operator to verify that light beam 38 is pulsed at the right frequency (this is especially useful when working with pulsed laser light), or to check other parameters of light beam 38.

OTHER TYPES OF LIGHT-GUIDING TIPS—FIGS. 4 to 7

FIG. 4 shows another geometrical solution of light-guiding terminal 34. This embodiment has a planar light-guiding tip 40" and convex output face 42'.

The geometrical shape of terminal 34 shown in FIG. 4 is different and so is its operation. Since tip 40" is planar beam 38 first undergoes uniform reflection downward without focussing. Then, at output face 42', which is convex, beam 38 is focussed at focal point F.

Figure 5:
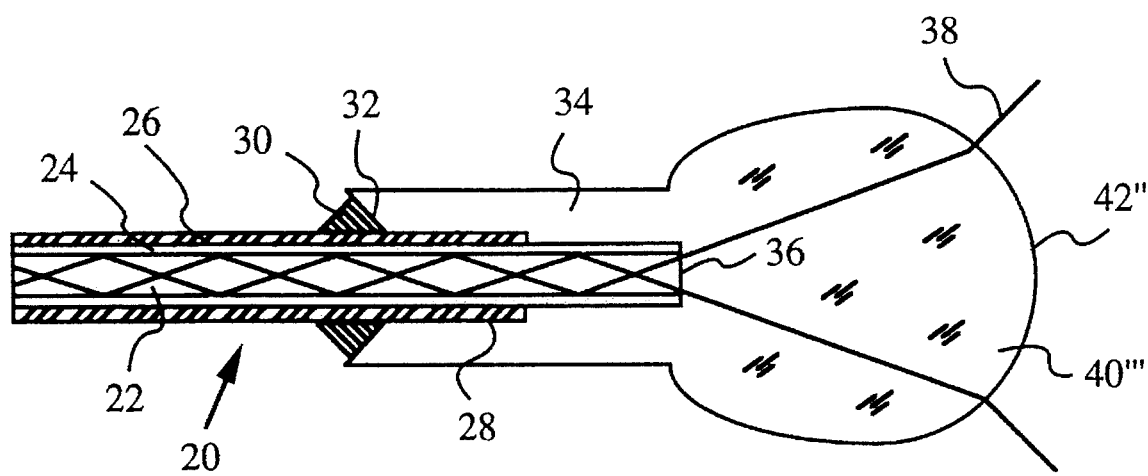
FIG. 5 is a side view of a light-guiding terminal for a single optical fiber with a light-scattering surface according to the invention.

In FIG. 5 light-guiding terminal 34 is oval and tip 40"' is rounded off in the shape of a bulb. There is no reflective coating. Output face 42" corresponds to the surface of tip 40"'. Terminal 34 has a rough or frosted surface capable of scattering light beam 38. Such frosting is preferably produced by grinding or otherwise abrading the surface of terminal 34. Scattering of beam 38 can also be achieved when the surface layer of terminal 34 is doped with a suitable doping agent, such as tiny particles of silver.

Terminal 34 with frosted surface shown in FIG. 5 acts to uniformly diffuse light beam 38 by scattering. Varying degrees of surface smoothness will produce different degrees of scattering.

Figure 6:
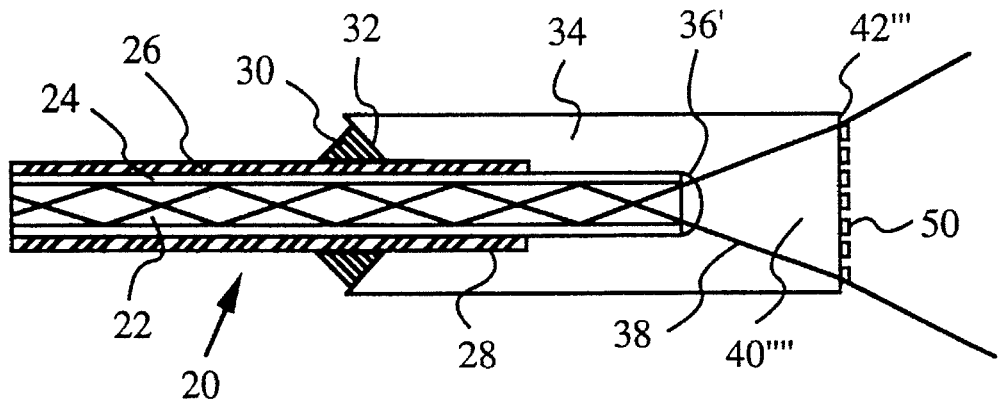
FIG. 6 is a side view of a light-guiding terminal for a single optical fiber with a concave fiber junction face and a diffraction pattern according to the invention.
Figure 7:
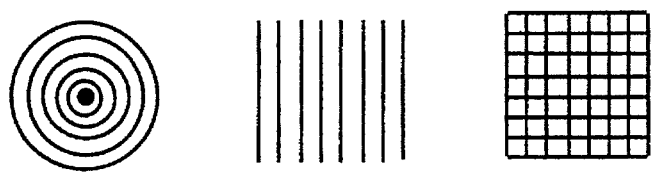
FIG. 7 shows three diagrams of exemplary diffraction patterns which can be used with the light-guiding terminal according to the invention.

In FIG. 6 input face 36 of terminal 34 is convex. Output face 42"' is flat and perpendicular to the direction of propagation of light beam 38. Light-guiding tip 40"" is rectangular. A diffraction pattern 50 covers output face 42"'. Various types of diffraction patterns 50 can be produced on face 42"' by conventional methods, e.g., raking or etching. FIG. 7 illustrates three exemplary grating patterns 50 for performing standard optical operations on light beam 38.

A different light guiding method is employed by terminal 34 shown in FIG. 6. Light beam 38 enters terminal 34 through convex face 36'. The latter focuses beam 38 on planar output face 42"'. In exiting through face 42"', beam 38 is focussed by diffraction pattern 50 at predetermined constructive interference nodes (not shown). Of course, any diffraction pattern 50 can be provided to appropriately guide and focus beam 38.

DESCRIPTION OF LIGHT-GUIDING TERMINALS FOR MULTIPLE OPTICAL FIBERS AND BUNDLES—FIGS. 8 to 12

Figure 8:
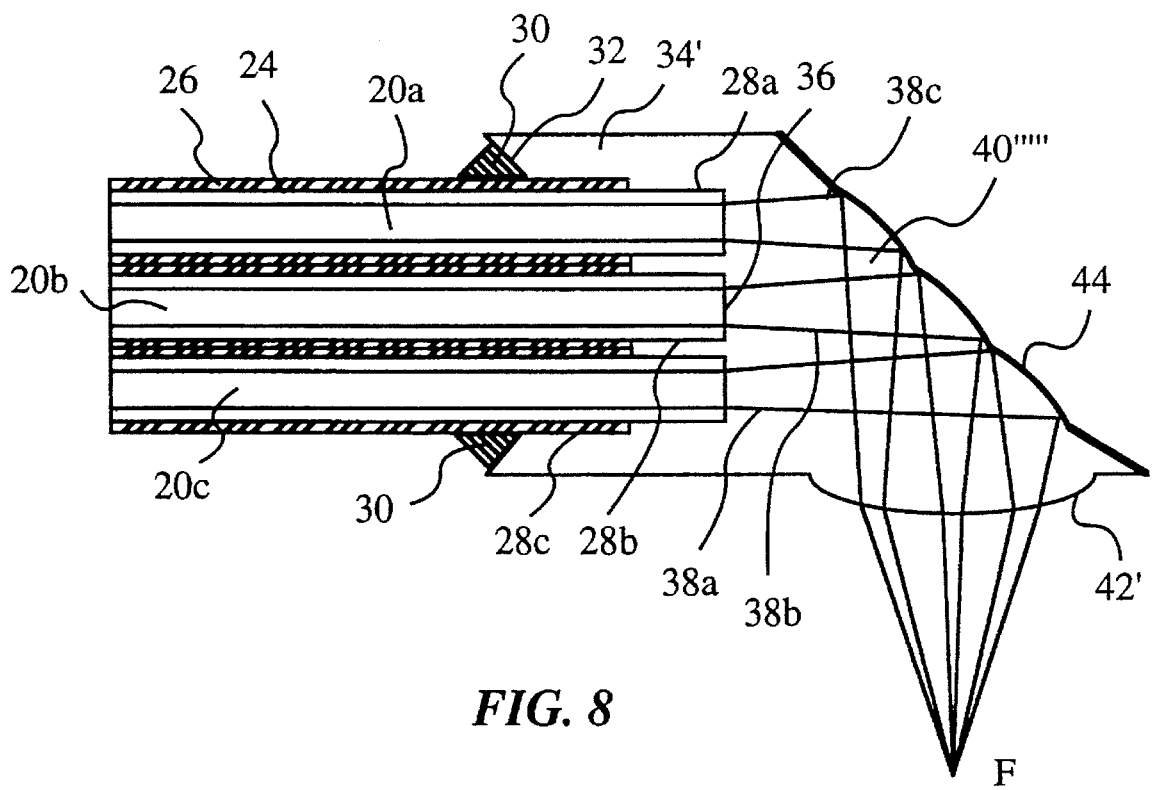
FIG. 8 is a side view of a light-guiding terminal according to the invention for splicing three optical fibers and focussing their light at one focal point.

It will be appreciated by one skilled in the art that minor modifications to any of the embodiments described above will allow to perform identical optical operations on fiber bundles rather than individual fibers. FIG. 8 shows an exemplary light-guiding terminal 34' adapted for receiving three optical fibers 20a, 20b, and 20c. Light-guiding tip 40"" exhibits three convex sections for deflecting and guiding diverging light beams 38a, 38b, 38c. Output face 42' is also convex, like in FIG. 4. Fibers 20a, 20b, and 20c are located inside corresponding ducts 28a, 28b, 28c and they are held in place by adhesive 30 inside space 32 and mutual traction. Of course, other attachment methods are possible, including placement of adhesive between individual optical fibers.

LIGHT-TERMINAL FOR FOCUS SHAPING—FIG. 9

Figure 9:
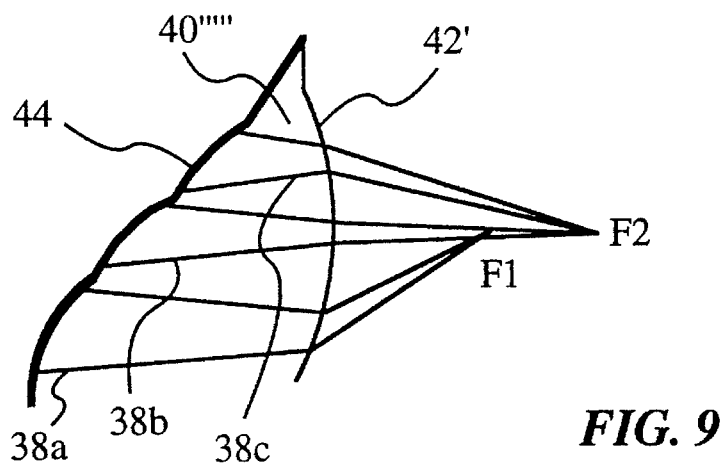
FIG. 9 is a side view of the tip portion of a light-guiding terminal for focussing three laser beams at two foci.

FIG. 9 is a side view of the tip portion of anther light-guiding terminal for three optical fibers (not shown). The curvatures of the reflecting sections of light-guiding tip 40"" are different than in the exemplary embodiment in FIG. 8. Output face 42' is convex.

LIGHT-TERMINAL FOR USE WITH AN OPTICAL CABLE—FIGS. 10 to 12

FIG. 10 shows an exemplary integrated optical cable 66 which can be used in conjunction with light-guiding terminal 34. Optical cable 66 includes a large-diameter power laser fiber 56 and a video fiber bundle 58 for image transmission. The diameter of power laser fiber 56 can range from less than a few millimeters to a centimeter or more. Video fiber bundle 58 consists of individual video fibers 20 shown in cross section in FIG. 11. A protective bundle collar 64 surrounds bundle 58. Both bundle 58 and power laser fiber 56 are embedded inside a light-transmitter bundle 54 consisting of individual optical fibers. The individual fibers of bundle 54 are embedded in a bonding epoxy resin 54 and their purpose is to deliver visible light for illumination. Fiber alignment pins 62a and 62b are wedged in on either side of bundle 54 to align optical fibers with laser fiber 56 and video fiber bundle 58. This ensures that light carried by power laser fiber 56, the fibers of bundle 58, and the fibers of bundle 54 are focussed on the same spot by light-guiding terminal 34 of FIG. 12. The method to achieve this effect is well-know to one skilled in the art.

In general, for high-resolution applications the number of optical fibers in bundles 58 and 54 should be as large as possible, e.g., several hundred or more. Finally, on the outside, cable 66 is enveloped by a protective sheath 60 of plastic material.

OPTICAL CABLE INSIDE LIGHT-GUIDING TERMINAL—FIG. 12

FIG. 12 illustrates cable 66 inserted into duct 28 of light-guiding terminal 34. For reasons of clarity, only some light beams 38a, 38b, 38c, etc. are traced.

OPERATION OF LIGHT-GUIDING TERMINALS FOR MULTIPLE OPTICAL FIBERS AND BUNDLES—FIGS. 8 to 12

While the above exemplary embodiments explain the functioning of various light-guiding terminals 34 for single fibers, analogous terminals 34' can also be used for multiple fibers. This is illustrated in FIG. 8, where light beams 38a, 38b, 38c of fibers 20a, 20b, and 20c enter terminal 34' through input face 30, are reflected by convex sections of tip 40'''', and focussed at focal point F by convex output face 42. Alternatively, the convex sections of tip 40 of terminal 34 shown in FIG. 9 focuses beams 38a, 38b, and 38c at two different foci F1 and F2.

In a particular application integrated optical cable 66 (FIG. 10) can be used to perform visually supervised laser surgery with the aid of terminal 34'. To achieve this, power laser fiber 56 delivers a high-energy beam 38a via terminal 34' (FIG. 12) to a focal point F coincident with the area of surgery. Here high-energy beam 38a performs the desired incision. Meanwhile, the fibers of light-transmitter bundle 52 deliver light 38b to illuminate focal point F. A portion of that light 38c is reflected back towards input face 42' of terminal 34'. Reflected light 38c carries an image of surgical area F. After re-entering tip 40'''' through output face 42' light 38c is reflected by reflective coating 44 to video fiber bundle 58. Thus an image of focal point F is transmitted back to the sender, where it can be projected and processed by appropriate image processing equipment (not shown).

SUMMARY, RAMIFICATIONS, AND SCOPE

The reader will thus see that I have provided a precision light-guiding terminals for optical fibers and optical fiber bundles. This light-guiding terminal can be mounted quickly, in one easy-to-follow step, and is sufficiently inexpensive to be considered disposable. In addition, the light-guiding terminal of the invention ensures proper beam alignment and provides stress relief at fiber ends. There is also no need to use additional optical elements or mechanical devices with the light-guiding terminal presented.

The geometry of the light-guiding terminal can be altered to perform virtually any optical operation formerly requiring a large number of optical elements. For example, the light-guiding tip can exhibit several forms of curvature at once, thus treating each portion of a light beam received differently. In addition, diffraction gratings can be provided at various locations on the surface of the terminal. Finally, the terminal can bemused with many fibers, fiber bundles, and cables to perform multiple optical tasks simultaneously using transmitted and reflected light. The materials, dimensions, shapes, and many other parameters can be changed as well.

Therefore, the scope of the invention should be determined, not by examples given, but by the appended claims and their legal equivalents.

We claim:

1. A precision light-guiding terminal for optical fibers comprising:

a) an insertion duct for receiving an end portion of an optical fiber;

b) an input face for in-coupling of light conducted by said optical fiber;

c) a non-planar tip portion for performing optical operations on Said light and for guiding said light, said tip portion containing a means for leaking a portion of said light;

d) a means for detecting said leaked portion of said light; and e) an output face for out-coupling said light.

2. The precision light-guiding terminal of claim 1 wherein said means for leaking a portion of said light comprises a hole and said means for detecting said leaked portion of said light comprises a photodiode.

3. A precision light-guiding terminal for optical fibers comprising:

a) an insertion duct for receiving an end portion of an optical fiber;

b) an input face for in-coupling of light conducted by said optical fiber;

c) a non-planar tip portion for performing optical operations on said light and for guiding said light; and d) an output face for out-coupling said light, said output face containing a diffraction grating for shaping and gutting said light.

4. A precision light-guiding terminal for optical fibers, said light guiding terminal having a toughened surface and comprising:

a) an insertion duct for receiving an end portion of an optical fiber;

b) an input face for in-coupling of light conducted by said optical fiber;

c) a non-planar tip portion for performing optical operations on said light and for guiding said light; and d) an output face for out-coupling said light.

5. A precision light-guiding terminal for optical fiber bundles comprising:

a) an insertion duct for receiving an end portion of an optical fiber bundle;

b) an input face for in-coupling of light conducted by said optical fiber bundle;

c) a non-planar tip portion for performing optical operations on said light and for guiding said light, said tip portion containing a grating for shaping and guiding said light; and d) an output face for out-coupling of said light.

6. A precision light-guiding terminal for optical fiber bundles comprising:

a) an insertion duct for receiving an end portion of an optical fiber bundle;

b) an input face for in-coupling of light conducted by said optical fiber bundle;

c) a non-planar tip portion for performing optical operations on said light and for guiding said light, said tip portion containing a means for leaking a portion of said light;

d) a means for detecting said leaked portion of said light; and e) an output face for out-coupling of said light.

7. The precision light-guiding terminal of claim 6 wherein said means for leaking a portion of said light comprises a hole and said means for detecting said leaked portion of said light comprises a photodiode.

8. A precision light-guiding terminal for optical fiber bundles comprising:
   a) an insertion duct for receiving an end portion of an optical fiber bundle;
   b) an input face for in-coupling of light conducted by said optical fiber bundle;
   c) a non-planar tip portion for performing optical operations on said light and for guiding said light; and
   d) an output face for out-coupling of said light, said output face containing a diffraction grating for shaping and guiding said light.

9. A precision light-guiding terminal for optical fiber bundles, said light guiding terminal having a roughened surface and comprising:
   a) an insertion duct for receiving an end portion of an optical fiber bundle;
   b) an input face for in-coupling of light conducted by said optical fiber bundle;
   c) a non-planar tip portion for performing optical operations on said light and for guiding said light; and
   d) an output face for out-coupling of said light.

* * * * *